(12) United States Patent
Müller et al.

(10) Patent No.: US 10,330,656 B2
(45) Date of Patent: Jun. 25, 2019

(54) APPARATUS FOR DETERMINING A MEASURED VALUE OF A MEASURAND IN PROCESS AUTOMATION TECHNOLOGY AND ITS METHOD OF USE

(71) Applicant: Endress+Hauser Conducta GmbH+Co. KG, Gerlingen (DE)

(72) Inventors: Frank Müller, Stuttgart (DE); Ralf Steuerwald, Eberdingen (DE); Thilo Krätschmer, Gerlingen (DE)

(73) Assignee: Endress+Hauser Conducta GmbH+Co. KG, Gerlingen (DE)

( * ) Notice: Subject to any disclaimer, the term of this patent is extended or adjusted under 35 U.S.C. 154(b) by 152 days.

(21) Appl. No.: 15/199,960

(22) Filed: Jun. 30, 2016

(65) Prior Publication Data
US 2017/0010248 A1   Jan. 12, 2017

(30) Foreign Application Priority Data

Jul. 8, 2015 (DE) .......................... 10 2015 111 057

(51) Int. Cl.
*G01N 33/18* (2006.01)
*G01N 21/59* (2006.01)
(Continued)

(52) U.S. Cl.
CPC ......... *G01N 33/1806* (2013.01); *G01F 11/28* (2013.01); *G01N 21/59* (2013.01); *G01N 21/78* (2013.01)

(58) Field of Classification Search
None
See application file for complete search history.

(56) References Cited

U.S. PATENT DOCUMENTS 4,705,667 A    11/1987  Marsoner et al.
2012/0173164 A1*  7/2012  Steuerwald ............ G01N 35/08
                                                             702/25

FOREIGN PATENT DOCUMENTS

CN    1882829 A    12/2006
CN   102498405 A    6/2012
(Continued)

OTHER PUBLICATIONS

Di-soric, Fork Light Barriers 2013, retrievved from internet: https://web.archive.org/web/20131221012706/https://www.di-soric.com/en/Fork-Sensor-Fork-Light-Barriers-di-soric-30468.html.*
(Continued)

*Primary Examiner* — Xiaoyun R Xu
(74) *Attorney, Agent, or Firm* — Mark A. Logan; PatServe

(57) ABSTRACT

The disclosure includes an apparatus for determining a measured value in a liquid medium, comprising at least a light transmitter, at least one light receiver assigned to the transmitter, a measuring chamber that can be filled with the medium, wherein an optical path runs through the measuring chamber from the transmitter to the receiver. The apparatus includes a dosing apparatus for dosing at least one reagent and/or the medium, and for inserting the dosed reagent and/or the medium into the measuring chamber. The dosing apparatus is designed as a tube, and the tube includes at least a first control point, wherein the volume in the tube from a starting point to a first control point defines the amount of reagent or medium to be inserted into the measuring chamber. The disclosure further includes the use of the apparatus and a method for dosing the reagent.

13 Claims, 4 Drawing Sheets

(51) Int. Cl.
      *G01N 21/78*     (2006.01)
      *G01F 11/28*     (2006.01)

(56) References Cited

FOREIGN PATENT DOCUMENTS

| CN | 103323608 A | 9/2013 |
| CN | 104713994 A | 6/2015 |
| DE | 3502546 A1 | 8/1985 |
| DE | 102009029305 A1 | 3/2011 |
| DE | 102013114138 A1 | 6/2015 |

OTHER PUBLICATIONS

Search Report for German Patent Application No. 102015111057.1, German Patent Office, dated Jan. 26, 2016, 6 pp.

\* cited by examiner

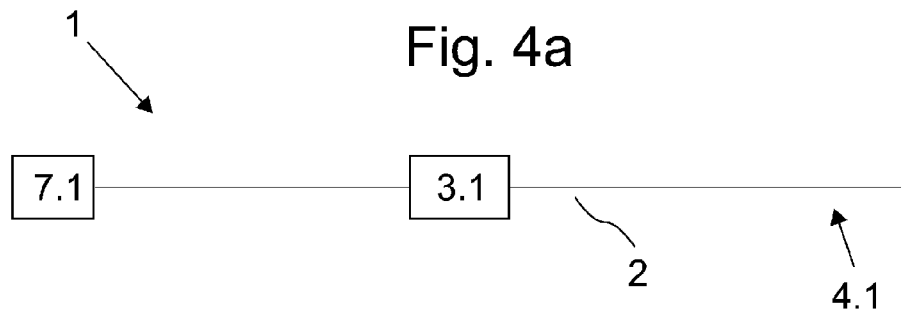
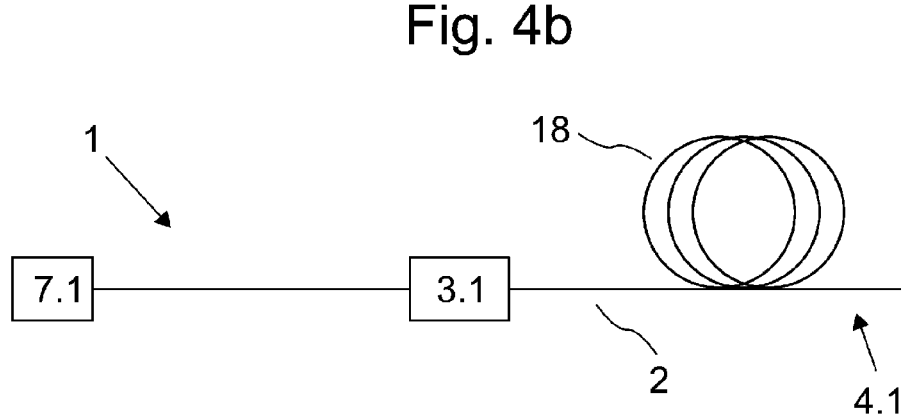
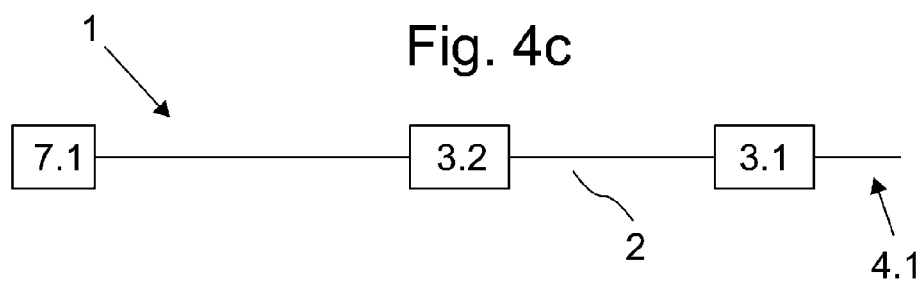
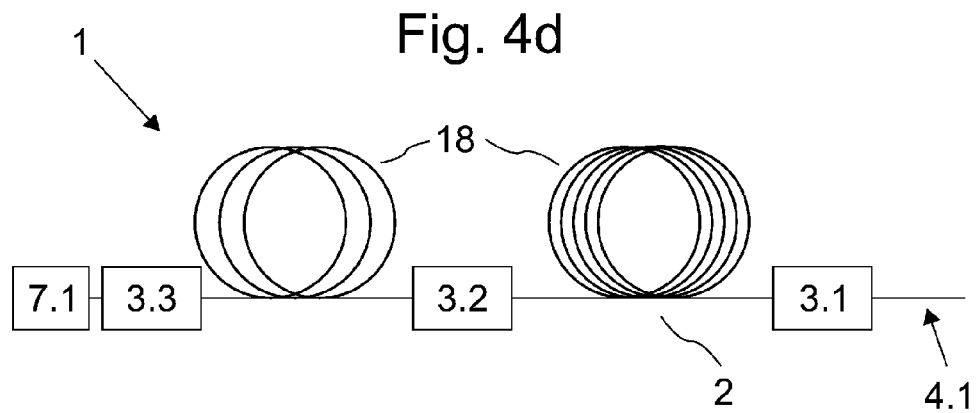

APPARATUS FOR DETERMINING A MEASURED VALUE OF A MEASURAND IN PROCESS AUTOMATION TECHNOLOGY AND ITS METHOD OF USE

CROSS-REFERENCE TO RELATED APPLICATIONS

The present application is related to and claims the priority benefit of German Patent Application No. 10 2015 111 057.1, filed on Jul. 8, 2015, the entire contents of which are incorporated herein by reference.

TECHNICAL FIELD

The invention concerns an apparatus for determining a measured value of a measurand in process automation technology in a liquid medium by means of an optical sensor. The invention further concerns a use of the apparatus in an analyzer, as well as a method for dosing at least one reagent for such an apparatus.

BACKGROUND

The term "analyzer" as used herein refers to a measuring apparatus in process automation engineering that measures certain substance contents with a wet-chemical method, such as, for example, the ion concentration in a medium that is to be analyzed. For that purpose, a sample is taken from the medium that is to be analyzed. Usually, the taking of the sample is performed by the analyzer itself in a fully automated fashion with the help of such means as pumps, hoses, valves, etc. For determining the substance content of a certain species, specific reagents that have been developed for the respective substance content and that are available in the housing of the analyzer are mixed with the sample that is about to be measured. In this way, a color reaction of the mixture is caused that is subsequently measured by an appropriate measuring device, such as, for example, a photometer. To be more precise, sample and reagents are mixed in a cuvette and then optically measured with different wavelengths using the transmitted light method. Thus, the measured value is determined by the receiver based upon light absorption and a deposited calibration model. Typical target measured values are, e.g., ammonia, total phosphate, chemical oxygen demand, and others.

It is extremely important to know the exact amount of different liquids that are being mixed with one another. For a correct determination of the substance content, it is required that the amount of the sample to be measured, as well as the amount of the reagents to be mixed into it, be precisely defined.

One option for measuring a certain quantity of liquid consists in a liquid container with a light barrier.

This method generally shows high accuracy and repeatability, is stable long-term, since the mechanically moved parts do not contribute to the accuracy of dosage, and easily renders itself for automation. As a standard procedure, a dosing tube made of glass is used, with a light barrier (LED and photo detector) for adjusting the correct dosage volume for the respective method attached at the suitable position. A sample or reagent liquid is introduced into the dosing tube via an apparatus, e.g., a piston pump, until the light barrier is triggered. Several light barriers may be attached to a dosing tube, in case several volumes must be dosed.

This method, however, also has several disadvantages: Inappropriate triggering of the light barrier causes erroneous dosings. This happens, for example, in case of drops of liquids that get caught on the dosing tube or move along the dosing tube wall. Liquid membranes that cover the cross-section of the dosing tube like a film may also erroneously trigger the light barrier.

Once arranged, a system with dosing tube and light barrier is very difficult to adapt and/or extend. This is due to the mechanical connection of the light barrier to the dosing tube, as well as the dosing tube cross section selected. In addition, it is impossible to position two light barriers very close to one another, due to the mechanical space demanded by the light barriers. More generally speaking, it is difficult to dose small volumes of liquid and large volumes of liquid in the same system. If the dosing tube is dirtied to a point that it cannot be cleaned anymore, it has to be exchanged. This exchange is often difficult to perform and requires trained staff.

BRIEF SUMMARY

The disclosure includes an apparatus for determining a measured value of a measurand in process automation technology in a liquid medium by means of an optical sensor, especially for the photometric capture of the contents of a substance in the medium. The apparatus includes at least one transmitter for transmitting transmitted light, at least one receiver associated with the transmitter for receiving received light, and a measuring chamber that can be filled with the medium. An optical measuring path runs through the measuring chamber from the transmitter to the receiver. The apparatus includes at least one dosing apparatus for the dosage of a certain amount of at least one reagent and/or the medium and for inserting the reagent and/or the medium into the measuring chamber. The apparatus includes a superordinate unit for generating an excitation signal for producing the transmitted light. The transmitted light is converted into the received light by means of interaction, especially by absorption, depending upon the measurand along the measuring path. The receiver generates a receiver signal from the converted received light, and the measured value is identifiable from the receiver signal. The dosing apparatus is designed as a tube, and the tube comprises at least a first control point, wherein at least the volume in the tub from a starting point to the first control point defines the amount of reagent or medium to be inserted into the measuring chamber. The tube of the dosing apparatus is designed as a tube made of polytetrafluorethylene.

The first control point of the dosing apparatus tube is designed as a first light barrier and the tube is designed transparently for the light of the light barriers. The light barrier is designed as a forked light barrier. The light barrier the light barrier is designed as an infrared light barrier with daylight filter. There may be two or more control points. The starting point is designed as a control point or as a point in the valve module The dosing apparatus tube includes at least one loop. The dosing apparatus includes at least one valve module on the first side, wherein the valve module is at least switchable between the medium, at least one reagent, and the measuring chamber. The dosing apparatus includes on a second side an air value for introducing air into the tube. The dosing apparatus includes also a pump, especially a syringe pump, for conveying the reagent.

In at least one embodiment, there is also a control unit which controls the dosage in a fully automated way, using signals from at least one control point.

In a further embodiment, the apparatus is used in an analyzer for determining a measured value of a measurand in process automation engineering, in particular, for analyzing at least one substance concentration.

Another aspect of the disclosure includes a method for dosing at least one reagent for an apparatus for determining a measured value of a measurand in process automation technology in a liquid medium by means of an optical sensor in a measuring chamber by means of a dosing apparatus designed as a tube, and the tube comprising at least one first control point, wherein the volume in the tube up to the first control point defines an amount of reagent and/or medium to be introduced into the measuring chamber, wherein the method includes the steps of: closing an air valve; opening a first valve with access to the reagent; closing a second valve with access to the measuring chamber; conveying the reagent to the first control point; opening the air valve and introducing air into the tube; closing the air valve; closing the first valve; opening the second valve; and conveying the reagent into the measuring chamber.

BRIEF DESCRIPTION OF THE DRAWINGS

The measuring system according to the invention in its entirety is marked with the reference symbol 1 and is shown in FIG. 1.

FIG. 4a shows a dosing apparatus of an apparatus according to an exemplary embodiment of the present disclosure.

FIG. 4b shows a dosing apparatus of an apparatus according to an alternative embodiment of the present disclosure.

FIG. 4c shows a dosing apparatus of an apparatus according to a further embodiment of the present disclosure.

FIG. 4d shows a dosing apparatus of an apparatus according to a further embodiment of the present disclosure.

In the figures, the same features are marked with the same reference symbols.

DETAILED DESCRIPTION

Figure 1:
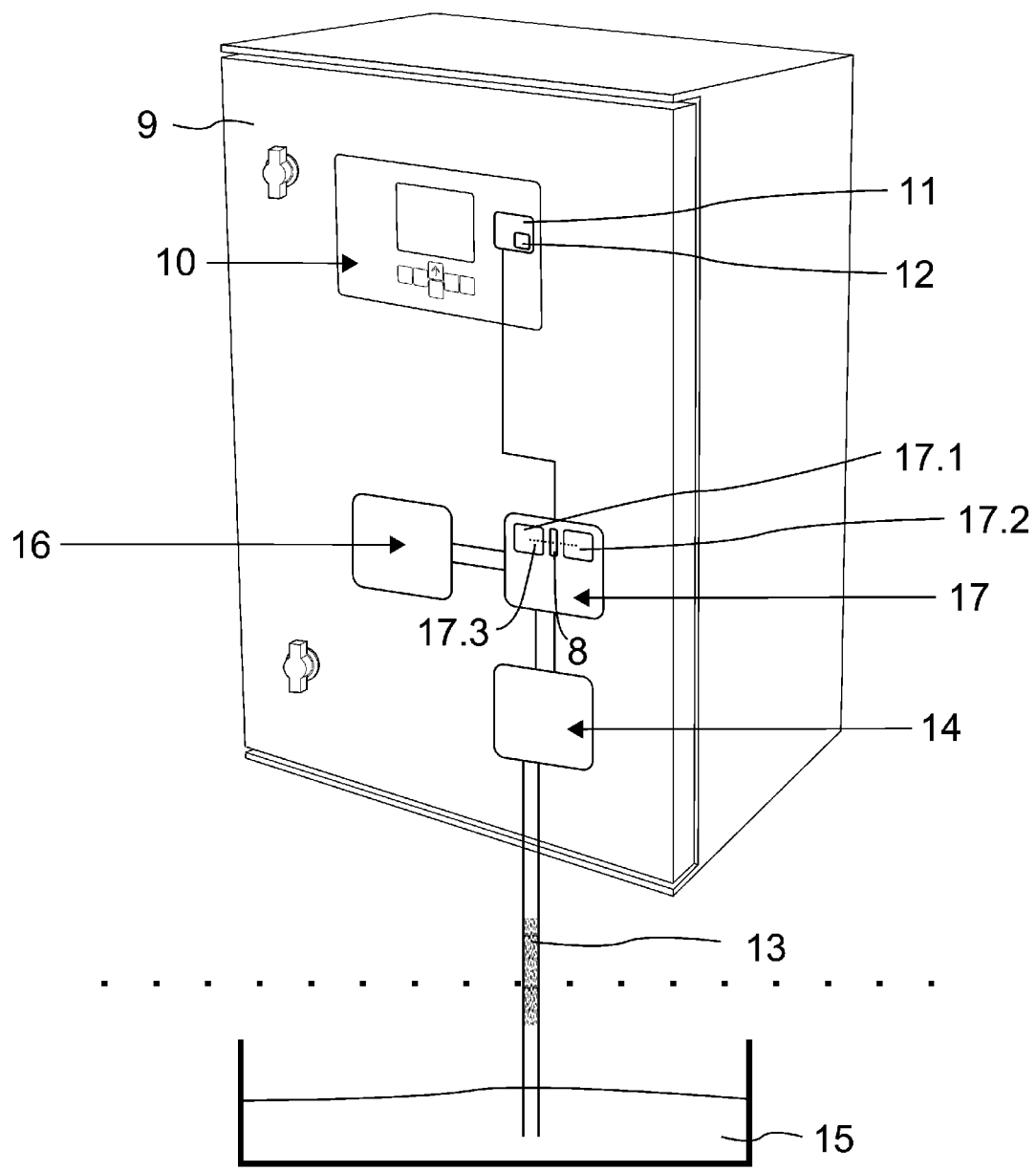
FIG. 1 shows an analyzer, including an embodiment of the present disclosure.

The disclosure provides a system for dosing liquids for wet-chemical analyzers that is economical, robust, easy to maintain, and flexible. This object is achieved by means of an apparatus comprising: at least one transmitter for transmitting transmitted light, at least one receiver associated with the transmitter for receiving received light, a measuring chamber that can be filled with the medium, with an optical measuring path running through the measuring chamber from the transmitter to the receiver, at least one dosing apparatus for dosing a certain amount of at least one reagent and/or the medium, and for inserting the reagent and/or the medium into the measuring chamber, and a superordinate unit for generating an excitation signal for producing the transmitted light, wherein the transmitted light is converted into the received light by means of interaction, especially by absorption, depending upon the measurand along the measuring path, wherein the receiver generates a receiver signal from the converted received light, and wherein the measured value is identifiable from the receiver signal. The apparatus is characterized in that the dosing apparatus is designed as a tube, and the tube comprises at least a first control point, wherein at least the volume in the tube from a starting point to a first control point defines the amount of reagent or medium to be inserted into the measuring chamber.

This allows quick and uncomplicated maintenance of the system, since the tube can be connected to the rest of the wet-chemical analyzer with conventional hose connectors. The dosage volume can easily be adjusted via the tube length. The components used render the apparatus inexpensive, flexible, easy to maintain, and robust.

In one advantageous further embodiment, the tube is designed of polytetrafluorethylene (PTFE), since this has a high chemical resistance and is also inexpensive to purchase.

Preferably, at least the first control point is designed as a first light barrier, and the tube is transparent for the light of the light barriers. A light barrier is a simple possibility for checking whether or not liquid is in the tube.

As an inexpensive option for a light barrier, the light barrier is designed as a forked light barrier.

For good detection results and an increased sensitivity to interference against daylight, the light barrier is designed as an infrared light barrier with daylight filter.

In one advantageous embodiment, the apparatus comprises two control points. The second control point, too, may be designed as a light barrier and/or forked light barrier. The light barrier may also be designed as an infrared light barrier with daylight filter. If one uses two control points, the volume to be dosed may be defined by the volume between the two control points. Alternatively, different volumes may be dosed in this way, since each volume is used up to the respective control points. In one embodiment, the second control point serves as a safety control point for detecting errors.

In order to be able to measure more liquid to be dosed in a small space, the tube comprises at least one loop. If several loops are used, the volume may be increased accordingly. For smaller volumes, a loop is not necessarily required; in certain applications such as the measuring of COD (chemical oxygen demand); this is, however, advantageous, due to the increased dosing volume. By increasing or decreasing the number of loops, the dosing volume in an existing device may be changed in a simple manner.

In one advantageous embodiment, the dosing apparatus on the first side comprises at least one valve module, with the valve module being at least switchable between the dosing apparatus, the at least one reagent, and the measuring chamber. Consequently, one may switch back and forth between the various sources of liquid and the measuring chamber in order to convey the respective liquid. The volume of the amount of reagent to be inserted is defined in one embodiment from the valve module to the first control point. If several control points are available, the respective distance from the valve module to the respective control point may serve as dosage.

In one preferred further development, the starting point is designed as a control point or as a point in the valve module. This defines the volume to be dosed.

In one preferred embodiment, the dosing apparatus on a second side comprises at least an air valve for introducing air into the tube. This air buffer may be conveyed. If medium or reagent are found in front of this air buffer, the air buffer may push the medium or reagent forward, e.g., up to the measuring chamber.

Preferably, and as a simple form of conveyance, the dosing apparatus comprises a pump—especially, a syringe pump for conveying the reagent.

In one advantageous embodiment, the apparatus comprises a control unit, with the control unit controlling the dosage fully automatically, using signals from at least one control point. No interaction from an operator is, therefore, required.

The object is further achieved by using at least one apparatus, as described above, in an analyzer for determining a measured value of a measurand in process automation technology—in particular, for determining at least one substance concentration in a medium.

The object is further achieved by a method for dosing at least one reagent for an apparatus for determining a measured value of a measurand in process automation technology in a liquid medium by means of an optical sensor in a measuring chamber by means of a dosing apparatus designed as a tube, and the tube comprising at least one first control point, wherein the volume in the tube up to the first control point defines an amount of reagent and/or medium to be introduced into the measuring chamber, wherein the method comprises the steps: closing an air valve, opening a first valve with access to the reagent and closing a second valve with access to the measuring chamber, conveying the reagent to the first control point, opening the air valve and introducing air into the tube, closing the air valve, closing the first valve and opening the second valve, and conveying the reagent into the measuring chamber.

The apparatus according to the invention is applied in an analyzer 9 in process automation engineering. The analyzer shall be described first.

To be measured is, for example, the direct absorption of a substance or the intensity of a color, which is created by converting the substance to be defined into a color complex by means of reagents. Further possible measured variables that function according to a similar principle are turbidity, fluorescence, etc. A further application example is the measurement of the chemical oxygen demand (COD), with COD being a sum parameter, which means that the measured value results from the sum total of the ingredients and, thus, cannot be attributed to one individual ingredient. Using this measuring method, one generates a color change in a reactor. Other possible parameters are, for example, the total carbon, total nitrogen, or an ion concentration, such as, for example, the concentration of the ions of ammonia, phosphate, nitrate, etc.

A sample 13 is taken from the medium 15 that is to be analyzed, which can be a liquid or a gas, for example. Usually, the taking of the sample 13 happens fully automatically with the help of subsystems 14, such as pumps, hoses, valves, etc. For determining the substance content of a certain species, one or several specific reagents 16 that have been developed for the respective substance content and that are available in the housing of the analyzer are mixed with the sample 13 that is about to be measured. In FIG. 1, this is shown in a symbolic manner. In reality, different vessels are provided with different reagents, which are extracted by means of the aforementioned pumps, hoses, and valves, etc., and possibly mixed. Likewise, for every process (taking the sample, mixing of reagents, etc.) separate pumps, hoses, and valves can be used.

In this way, a color reaction of the mixture is caused that is then measured by means of an appropriate measuring device, such as, for example, a photometer 17. For that purpose, for example, the sample 13 and the reagents 16 are mixed in a measuring chamber 8 and optically measured with light of at least one wavelength using the transmitted light method. In case COD or phosphate ions are identified, one wavelength is used; however, there are also methods that use at least two different wavelengths. To that end, light is transmitted through the sample 13 by a transmitter 17.1. A receiver 17.2 for receiving the transmitted light is assigned to the transmitter 17.1, with an optical measuring path 17.3 proceeding from the transmitter 17.1 to the receiver 17.2 (in FIG. 1, indicated by a dotted line). The transmitter 17.1 comprises, for example, one or several LED's, i.e., one LED per wavelength or an appropriate light source with broadband stimulation. Alternatively, a broadband light source fitted with an appropriate filter is used. Typical wavelengths range from infrared to ultra-violet, i.e., from approximately 1100 nm to 200 nm. The receiver 17.2 can comprise one or more photo diodes.

The measured value is created by the receiver based upon light absorption and a stored calibration feature. In case of COD measuring, the measured value is generated by a color change as mentioned above. At the beginning, the sample 13 is mixed with reagents 16, and a base measurement is conducted. Then additional reagents 16—namely, sulfuric acid—is added and the mixture heated to accelerate the reaction. After a certain time, a plateau measurement is conducted. The travel is determined from plateau and base measurement, and, together with the stored calibration curve, results in the measured value.

Figure 3:
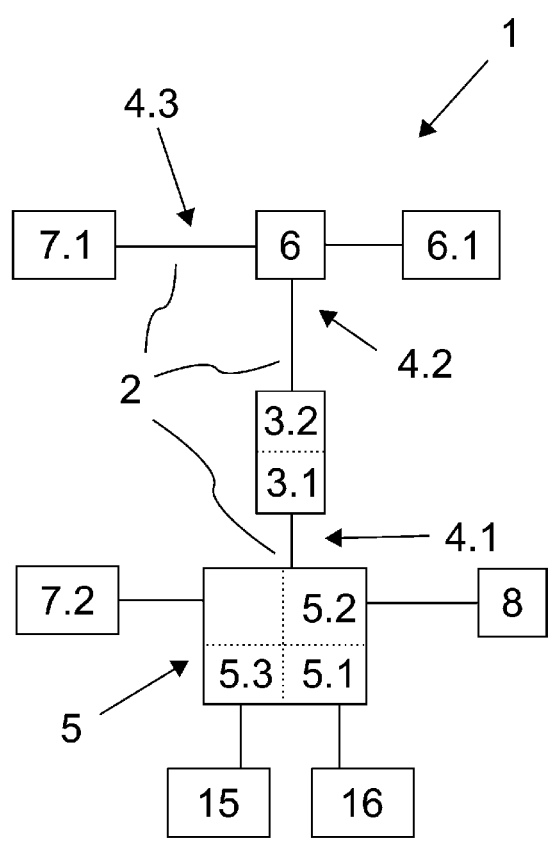
FIG. 3 is a schematic diagram of the parts of the analyzer that are relevant for the dosing.

Furthermore, the analyzer 9 comprises a transmitter 10 with a microcontroller 11, along with a memory 12. The analyzer 9 can be connected to a field bus via the transmitter 10. Furthermore, the analyzer 9 is controlled via the transmitter 10. Thus, the extraction of a sample 13 from the medium 15, for example, is triggered by the microcontroller 11 by sending appropriate commands to the subsystems 14. Likewise, the measurement by the photometer 17 is controlled and regulated by the microcontroller. The dosing of probe 13 may also be controlled by the transmitter 10. In one embodiment, the dosing occurs in a fully automated manner by using the signals from the control points 3.1, 3.2, and 3.3, as shown in FIG. 3.

The process of extracting the sample 13 is described in principle below and schematically illustrated in FIG. 3. For extracting the sample 13 from the medium 15, a sample extracting system (not shown) is used that can, for example, comprise a pump 7.2. Through a medium pipeline, the sample 13 arrives in a container 1, also referred to as dosing apparatus 1 below. As mentioned above, the analyzer 9 comprises liquid containers that contain reagents to be added to the sample 13 for determining the measured variable of the analyzer 9 and standard solutions for calibrating and/or adjusting the analyzer 9.

The containers containing the reagents 16 are connected with the dosing apparatus 1 via fluid lines. In the present invention, the dosing apparatus 1 is designed as a tube 2. More precisely, the tube 2 is designed as a semi-transparent tube. In principle, any semi-transparent plastic is suitable as the material for this tube 2, if a high chemical resistance is required, e.g., Teflon (PTFE). The tube 2 is at least semi-transparent to the light of the light barrier (see below), as well as having chemical resistance to the medium 15 and the reagents 16. One example to be mentioned is a chemical resistance to sulfuric acid at 50 percent. The tube 2 has a cross-section of some millimeters, e.g., 3 mm.

The tube 2 is placed into a light barrier 3.1, especially into a forked light barrier, wherein this latter is equipped with at least one photo transistor, or, in a preferred embodiment, with two photo transistors. The light barrier 3.1 serves as a control point. The light barrier is designed as an infrared light barrier with daylight filter.

Figure 2:
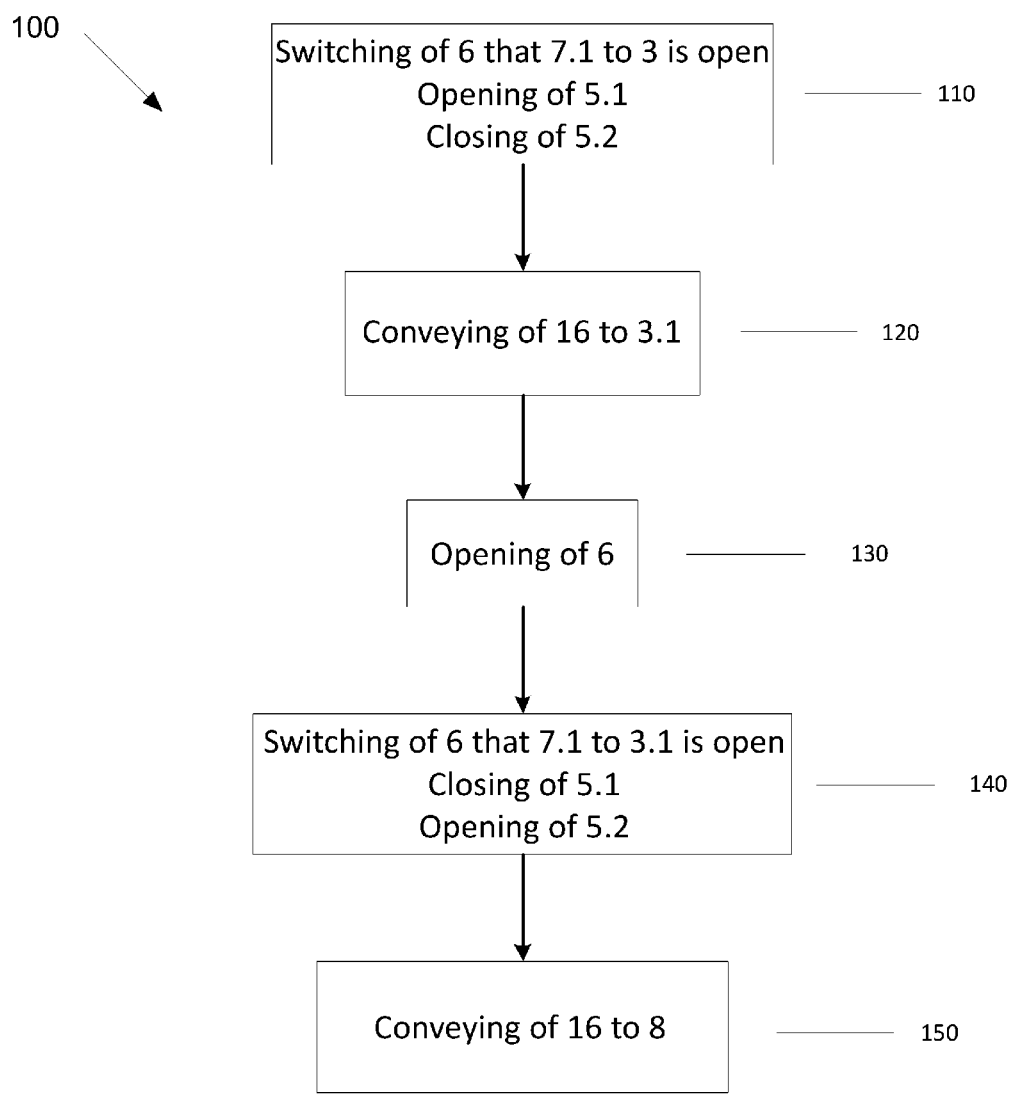
FIG. 2 shows the process sequence for dosing a reagent according to exemplary embodiments of the present disclosure.

The dosage volume can be adjusted via the tube length. FIG. 2 shows the method 100 according to the invention for dosing the reagent 16. FIG. 3 shows the basic structure of those parts of the analyzer 9 relevant for the dosage, while FIG. 4 shows various embodiments of the dosing apparatus 1.

As shown in FIGS. 2 and 3, at a step 110 of the method 100 according to the invention, an air valve 6 is inserted. The air valve 6 is designed as a three-port, two-position valve. The three-port, two-position valve 6 is switched in such a way that the channel from a first pump 7.1 to the tube 2 is open, a first valve 5.1 with access to the reagent 16 is opened, and a second valve 5.2 with access to the measuring chamber 8 is closed. Method 100 includes a step 120 where reagent 16 is conveyed to the first control point 3.1. Method 100 further includes a step 130 where the air valve 6 is opened, and air 6.1 introduced into the tube. Thus, an air buffer is introduced into the tube 2 on a third side 4.3. Method 100 includes a step 140 in which the air valve 6 is switched again, so that the channel is open from the first pump 7.1 to the first control point 3.1, the first valve 5.1 with access to the reagent 16 is also closed, and the second valve 5.2 with access to the measuring chamber 8 is opened. Method 100 further includes a step 150 in which the reagent 16 is conveyed into the measuring chamber 8. The reagent 6 is thus introduced into the measuring chamber 8 by means of an air buffer.

The dosing apparatus 1 comprises a pump 7.1—especially, a syringe pump—for conveying the reagent 16. The dosing apparatus 1 further comprises a pump 7.2—especially, a hose pump for conveying the medium 15. A hose pump 7.2 is used, since larger dosing volumes must be processed here in order to process the dead volume up to medium 15. An embodiment with only one pump may, however, be realized without any great technical effort.

The dosing apparatus 1 further comprises a valve module 5 on a first side 4.1. The valve module 5 has a first access 5.1 to the reagents 16, a second access 5.2 to the measuring chamber 8, and a third access 5.3 to the medium 15. On a second side 4.2, the dosing apparatus 1 comprises an air valve 6 with an air inlet 6.1 for introducing air into the tube 2. On a third side 4.3, the dosing apparatus 1 comprises a pump 7.1 for conveying reagents, medium, and/or air. As an exemplary illustration, FIG. 4 shows the dosing apparatus 1 with a first control point 3.1 and a second control point 3.2. As shown below, there are also embodiments with only one control point 3.1 or several control points.

Since the valve module 5 also has access to the medium 15, the medium 15 may also be conveyed to the measuring chamber 8 in a similar process, as described above.

The embodiment shown in FIG. 4a comprises a first light barrier 3.1, in addition to the pump 7.1. The amount of reagent 16 to be conveyed is defined by the volume in the tube 2 on the first side 4.1 from the valve module 5 to the first control point 3.1.

In an embodiment as shown in FIG. 4b, the dosing apparatus 1 comprises a tube 2 on a first side 4.1 with a loop 18. By arranging the tube 2 as a loop 18, a large quantity of volume may be housed in a small space. The more loops 18 that are created, the higher the volume. Accordingly, the volume may also be modified by the cross-section of the loops. For example, three loops may be made as shown. The cross-section of the loops is a few centimeters, e.g., 8 cm. The tube length in total ranges from a few centimeters up to a few meters, e.g., from about 30 cm up to 2 m. This allows volumes of a few milliliters, e.g., of 2-8 ml to be conveyed.

In this example, the volume is again defined from the valve module 5 to the first control point 3.1.

An alternate embodiment, as shown in FIG. 4c, comprises two light barriers 3.1 and 3.2. In this way, several volumes may be measured. The example shown allows at least two different volumes: from valve module 5 on the first side 4.1 to the first control point 3.1, and from the valve module 5 on the first side 4.1 to the second control point 3.2. Furthermore, a third volume from the first control point 3.1 to the second control point 3.2 may be generated by dosing by means of an air buffer generated by the valve module 5. Alternatively, the apparatus in FIG. 4c works like the apparatus in FIG. 4b, except that the second control point 3.2 acts as a safety control point for switching off in case of errors. The distances between the pump 7.1, the first control point 3.1, and the second control point 3.2 do not have to be equal.

FIG. 4d shows an embodiment including three control points 3.1, 3.2, and 3.3. Different loops 18 of the tube 2 are placed between the first control point 3.1 and the second control point 3.2, as well as between the second control point 3.2 and the third control point 3.3. The respective number of loops does not have to be equal; in the example, there are three or five respectively. In this example, a larger volume than in the other examples may be conveyed.

Naturally, any combination of the loops 18 and control points are possible, and the illustration is to be understood as an exemplary illustration.

The system described above is robust against an erroneous triggering of the light barriers 3.1, 3.2, 3.3, since the tube cross-section is too small to develop drops or films of liquid. Air pockets may also be identified and compensated for. For example, if one obtains the following measuring signal:

000000000001100000000000001111111111111, wherein "0" is a signal in case of liquids, and "1" is a signal for air, the underlined signal sequence "11" can unambiguously be identified as an air pocket, and, if necessary, be compensated for accordingly.

In addition, the system can be serviced quickly and without complication, since the tube can be connected to the rest of the wet-chemical analyzer with conventional hose connectors.

Thus, a wet-chemical analyzer 9 can be provided that has an inexpensive, flexible, easy to maintain, and robust design.

The invention claimed is:

1. An apparatus for determining a measured value of a measurand in a liquid medium, comprising:
   an optical transmitter for transmitting light, wherein the optical transmitter includes a light source;
   an optical receiver associated with the optical transmitter and configured to receive light transmitted by the optical transmitter and to generate a receiver signal based on the received light;
   a measuring chamber, wherein an optical measuring path extends through the measuring chamber from the optical transmitter to the optical receiver;
   a dosing apparatus structured to generate a first dosage of at least one reagent and a first dosage of the liquid medium and to provide the first dosage of the at least one reagent and the first dosage of the liquid medium into the measuring chamber, wherein the dosing apparatus includes a tube, a first light barrier disposed about the tube at a first control point, and a valve module switchable between the at least one reagent, the liquid medium, and the measuring chamber, wherein the tube is transparent to the light of the first light barrier, and wherein the tube is connected with the valve module, and a first volume of the tube from the valve module to the first control point defines the first dosage of the at least one reagent and the first dosage of the liquid medium to be provided into the measuring chamber; and a transmitter including a microcontroller and a memory, wherein the transmitter is configured to control the optical transmitter and the optical receiver, to generate the first dosage of the at least one reagent and the first dosage of the medium based on signals from the first light barrier, and to determine the measured value from the receiver signal wherein the transmitted light is converted into the received light by means of interaction along the measuring path in the measuring chamber with the at least one reagent and the medium.

2. The apparatus of claim 1, wherein the tube of the dosing apparatus is made of polytetrafluorethylene.

3. The apparatus of claim 1, wherein the first light barrier is a forked light barrier.

4. The apparatus of claim 1, wherein the first light barrier is an infrared light barrier having a daylight filter.

5. The apparatus of claim 1, wherein the dosing apparatus further includes a second light barrier disposed about the tube at a second control point, wherein the dosing apparatus is further structured to generate a second dosage of the at least one reagent and a second dosage of the liquid medium and to provide the second dosage of the at least one reagent and the second dosage of the liquid medium into the measuring chamber, and wherein a second volume of the tube from the valve module to the second control point defines the second dosage of the at least one reagent and the second dosage of the liquid medium to be provided into the measuring chamber.

6. The apparatus of claim 1, wherein the tube of the dosing apparatus includes at least one loop.

7. The apparatus of claim 1, wherein the dosing apparatus includes at least one air valve configured to introduce air into the tube.

8. The apparatus of claim 1, wherein the dosing apparatus includes a pump for conveying the at least one reagent.

9. The apparatus of claim 1, wherein the apparatus is employed in an analyzer for determining a measured value of a measurand in a process automation engineering application.

10. The apparatus of claim 1, wherein the apparatus is employed in an analyzer and wherein the measurand is at least one substance concentration.

11. The apparatus of claim 1, wherein the transmitted light is converted into the received light by means of absorption along the measuring path in the measuring chamber with the at least one reagent and the medium.

12. The apparatus of claim 8, wherein the pump is a syringe pump.

13. The apparatus of claim 5, wherein the dosing apparatus includes at least one air valve configured to introduce air into the tube, wherein the dosing apparatus is further structured to generate a third dosage of the at least one reagent and a third dosage of the liquid medium and to provide the third dosage of the at least one reagent and the third dosage of the liquid medium into the measuring chamber, and wherein a third volume of the tube from the first control point to the second control point defines the third dosage of the at least one reagent and the third dosage of the liquid medium to be provided into the measuring chamber.

* * * * *